United States Patent
Kuo et al.

(10) Patent No.: US 7,784,678 B2
(45) Date of Patent: Aug. 31, 2010

(54) ANALYTICAL STRIP READING APPARATUS WITH A REMOVABLE FIRMWARE DEVICE

(75) Inventors: Chien-Chih Kuo, Hsinchu (TW); Wen-Pin Hsieh, Hsinchu (TW)

(73) Assignee: ACTherm Inc., Hsinchu (TW)

( * ) Notice: Subject to any disclaimer, the term of this patent is extended or adjusted under 35 U.S.C. 154(b) by 0 days.

(21) Appl. No.: 12/423,349

(22) Filed: Apr. 14, 2009

(65) Prior Publication Data

US 2010/0140341 A1 Jun. 10, 2010

(30) Foreign Application Priority Data

Dec. 5, 2008 (WO) .............. PCT/CN2008/001978

(51) Int. Cl.
*G06F 17/00* (2006.01)
*G01N 21/00* (2006.01)
*G01N 27/00* (2006.01)
*G01N 21/03* (2006.01)
*G01N 1/00* (2006.01)

(52) U.S. Cl. .................. 235/375; 422/58; 422/61; 422/63; 422/81; 422/82.01; 422/82.02; 422/82.06; 422/98; 436/164; 436/165; 436/174; 436/178; 436/149; 600/300

(58) Field of Classification Search ............... 235/375; 422/58, 61, 81, 63, 68.1, 82.01, 82.02, 82.06, 422/98; 436/164, 165, 174, 178, 149
See application file for complete search history.

(56) References Cited

U.S. PATENT DOCUMENTS

| | | | |
|---|---|---|---|
| 4,608,231 A | 8/1986 | Witty et al. | |
| 4,675,299 A | 6/1987 | Witty et al. | |
| 4,678,752 A | 7/1987 | Thorne et al. | |
| 4,873,633 A | 10/1989 | Mezei et al. | |
| 5,126,952 A | 6/1992 | Kildal-Brandt et al. | |
| 5,128,105 A | 7/1992 | Berthold et al. | |
| 5,229,074 A | 7/1993 | Heath et al. | |
| 5,281,395 A | 1/1994 | Markart et al. | |
| 5,316,726 A | 5/1994 | Babson et al. | |
| 5,374,395 A | 12/1994 | Robinson et al. | |
| 5,445,147 A | 8/1995 | Schoendorfer et al. | |
| 5,798,035 A | 8/1998 | Kirk et al. | |

(Continued)

FOREIGN PATENT DOCUMENTS

| | | |
|---|---|---|
| CN | 2739639 | 11/2005 |
| CN | 201005780 | 1/2008 |
| CN | 201117004 | 9/2008 |
| EP | 0299521 A2 | 1/1989 |

*Primary Examiner*—Michael G Lee
*Assistant Examiner*—Laura Gudorf
(74) *Attorney, Agent, or Firm*—Ming Chow; Sinorica, LLC

(57) ABSTRACT

A detecting strip reader with a removable firmware device, comprising a detecting strip reader and a firmware device. The firmware device comprises a first electrical connecting end, a database module, and an operation module, the firmware device being removably electrically connected to a second electrical connecting end in the detecting strip reader via the first electrical connecting end, wherein the characteristic of detecting strip reader is in that: a plurality of light reaction equations of detecting strips are saved in the database module, and when the first electrical connecting end of the firmware device receives an input signal from the second connecting end, the operation module selects one specific light reaction equation from the plurality of light reaction equations saved in the database module and performs the operation of the specific light reaction equation.

22 Claims, 3 Drawing Sheets

U.S. PATENT DOCUMENTS

| | | |
|---|---|---|
| 5,822,071 A | 10/1998 | Dossman et al. |
| 5,885,529 A | 3/1999 | Babson et al. |
| 5,885,530 A | 3/1999 | Babson et al. |
| 5,902,982 A | 5/1999 | Lappe |
| 5,929,422 A | 7/1999 | Lappe |
| 6,036,092 A | 3/2000 | Lappe |
| 6,097,025 A | 8/2000 | Modlin et al. |
| 6,120,733 A | 9/2000 | Goodman et al. |
| RE37,194 E | 5/2001 | Kirk et al. |
| 6,269,313 B1 | 7/2001 | Givens et al. |
| 6,319,668 B1 | 11/2001 | Nova et al. |
| 6,656,428 B1 | 12/2003 | Clark et al. |
| RE38,509 E | 5/2004 | Lappe |
| 6,770,487 B2 | 8/2004 | Crosby |
| 6,830,731 B1 | 12/2004 | Buechler et al. |
| 6,867,051 B1 | 3/2005 | Anderson et al. |
| 7,064,823 B2 | 6/2006 | Roche et al. |
| 7,368,281 B2 | 5/2008 | Mozdy et al. |
| 7,390,458 B2 | 6/2008 | Burow et al. |
| 7,416,700 B2 | 8/2008 | Buechler et al. |
| 7,427,380 B2 | 9/2008 | McNeil et al. |
| 2004/0162988 A1 | 8/2004 | Harper |

ANALYTICAL STRIP READING APPARATUS WITH A REMOVABLE FIRMWARE DEVICE

BACKGROUND OF THE INVENTION

1. Field of the Invention

The present invention relates to an analytical strip reading apparatus, and more particularly, to an analytical strip reading apparatus applied for biological detection of photoreaction signal and to an analytical strip reading apparatus with a removable firmware device.

2. Description of the Prior Art

To meet the needs of humans to monitor chronic diseases, apparatus manufacturers have developed various kinds of detecting apparatuses to be applied in medical care, for example, blood glucose meter and electronic sphygmomanometers. Among all biochemical or immunological detecting apparatuses, the more common ones are those for detecting blood glucose, uric acid, or total cholesterol. Such kinds of detecting systems can be divided into optical reaction systems and electrochemical systems, wherein the electrochemical systems are cheaper and more frequently used.

However, no matter for biochemical or immunological detection, the right type of analytical strip is required to be used for performing tests. For example, blood glucose strip is required to be used for blood glucose tests while total cholesterol strip is required to be used for total cholesterol tests. In addition to selecting the right type of analytical strip, the next step is confirming the accuracy of lot number and expiration date on the container of strip. After the analytical strip is inserted into the detecting apparatus, the calibration information of reagent is then input into the machine, the step of which is performed due to that there may be some difference between calibration parameters of analytical strips manufactured in different lots. However, the aforementioned way of performing detection is under below risks: 1. the analytical strip used may belong to a wrong type; 2. the analytical strip used may have already passed its expiration date; 3. the analytical strip may bear a different lot number. The situations described above are all errors that are not allowed to happen as these errors will compromise the accuracy of test results.

Moreover, with the progress of the biotechnology industry and the advancement of detection techniques, analytical strips for different bio-makers have continuously been developed and thus new types of analytical strips cannot be used in existing detecting apparatuses. In order to solve this problem, the conventional solution is that the users are requested to send the detecting apparatuses back to the manufacturers or the commercial agents for the manufacturers or the commercial agents to perform updates and then send the machines back to the users for further use, this way of service thus causing inconvenience and disturbance of users when using the machines.

SUMMARY OF THE INVENTION

In order to make improvements and solve the aforementioned problems of the prior art, one principal objective of the present invention is to provide an analytical strip reading apparatus, wherein built-in barcode reader reads barcode information on the analytical strip, automatic detection is performed to obtain calibration information of type, lot number, expiration date, and lot of analytical strip, and a corresponding optical reaction equation is selected from the database sub-module to perform specific detecting procedure. Thus, manual operation errors that compromise the accuracy of test results can be effectively avoided.

Another principal objective of the present invention is to provide an analytical strip reading apparatus with an input keyboard, thereby further providing a function of manual input.

Still another principal objective of the present invention is to provide an analytical strip reading apparatus with a removable firmware device, wherein firmware program can be updated by replacing firmware device and thus the risks incurred during transportation of analytical strip reading apparatus and time spent on transportation can be eliminated to facilitate operation of users.

Yet another principal objective of the present invention is to provide an analytical strip reading apparatus with a removable firmware device, wherein firmware device is validated and provided by manufacturer or commercial agent to guarantee the completeness of data in firmware device for ensuring the stability of analytical strip reading apparatus and accuracy of test results.

And still another principal objective of the present invention is to provide an analytical strip reading apparatus with a removable firmware device, wherein the database of optical reaction equations can be updated by replacing firmware device to further ensure the accuracy of test results.

In view of the aforementioned objectives, the present invention first provides an analytical strip reading apparatus, comprising a housing and a monitor provided on the housing; a delivering device for supporting an analytical strip to deliver the analytical strip into or out of the housing; a barcode reader provided in the housing for reading barcode information of the analytical strip; a reaction signal reader provided in the housing for reading photoreaction signal of the analytical strip; and a mother board provided in the housing for electrically connecting the monitor, the delivering device, the barcode reader, and the reaction signal reader, wherein the characteristic of the analytical strip reading apparatus is in that: an input keyboard provided on the housing and a firmware device provided on the mother board are further comprised, and the firmware device performs detection after an identification code is input via the input keyboard, the firmware device comprising: a database sub-module with optical reaction equations of a plurality of types of analytical strips saved therein, and a process sub-module selecting a corresponding optical reaction equation of analytical strip from the database sub-module and performing the process according to the photoreaction signal of the analytical strip as provided by the reaction signal reader to come out a test result.

The present invention then provides an analytical strip reading apparatus with a removable firmware device, comprising an analytical strip reading apparatus and a removable firmware device. The firmware device comprises a first electrical connecting terminal, a database sub-module, and a process sub-module, the firmware device being removably electrically connected to a second electrically connecting terminal in the analytical strip reading apparatus via the first electrically connecting terminal, wherein the characteristic of the analytical strip reading apparatus is in that: optical reaction equations of a plurality of analytical strips are saved in the database sub-module, and when the first electrical connecting terminal of the firmware device acquires an input signal from the second connecting terminal, the process sub-module selects a corresponding optical reaction equation from the database sub-module and performs the process to come out the result.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention discloses an analytical strip reading apparatus in which the fundamental structures and principles of biological detection, analytical strip related, and mechanical operation employed are well known to those of ordinary skill in the art. Therefore, a detailed description of such principles and mechanisms will be omitted herein for brevity. Besides, the drawings referred to herein are not drawn according to actual dimensions and need not be so because they are intended to demonstrate features of the present invention only schematically.

Figure 1A:
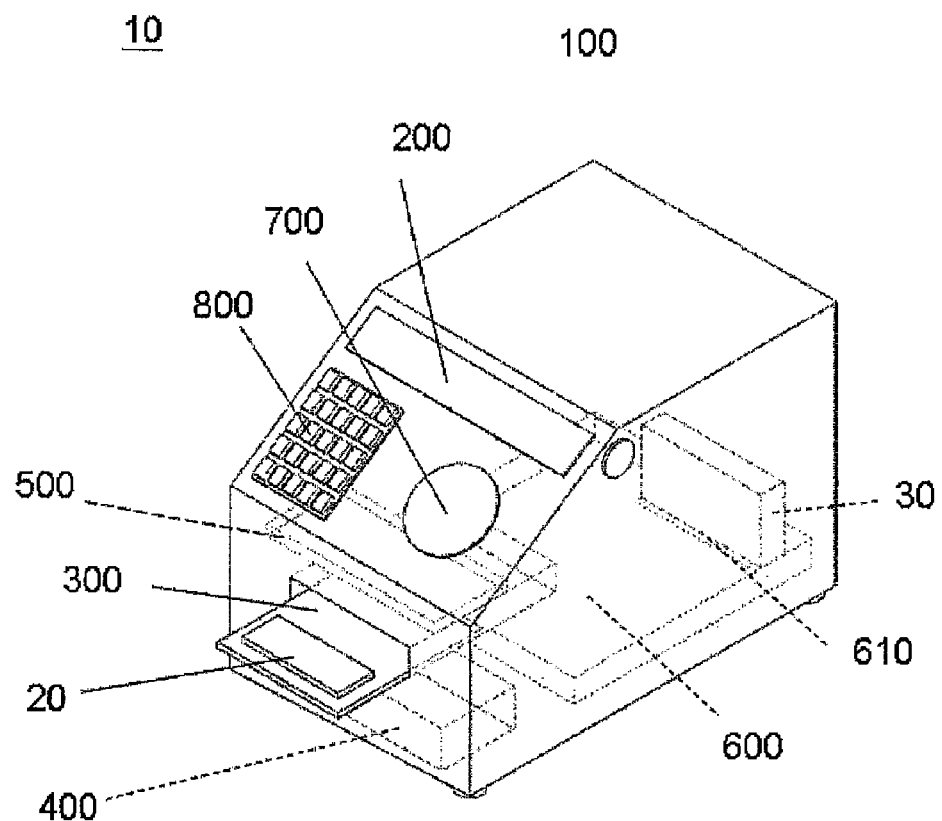
FIG. 1A is a perspective view of an analytical strip reading apparatus according to the present invention as observed from the front.

Please first refer to FIG. 1A for a view of analytical strip reading apparatus according to the present invention. As shown in FIG. 1A, the analytical strip reading apparatus 10 comprises: a housing 100, a monitor 200, a delivering device 300, a barcode reader 400, a reaction signal reader 500, a mother board 600, a switch 700, an input keyboard 800, and an interface 900. In the present embodiment, the monitor 200, delivering device 300, barcode reader 400, reaction signal reader 500, switch 700, input keyboard 800, and interface 900 in the analytical strip reading apparatus 10 can all be electrically connected to the mother board 600 via flexible bus. Of course, the monitor 200, delivering device 300, barcode reader 400, reaction signal reader 500, switch 700, input keyboard 800, and interface 900 in the analytical strip reading apparatus 10 can all be fixedly electrically connected to the mother board 600 directly. What are described above are all embodiments of the present invention.

Figure 1B:
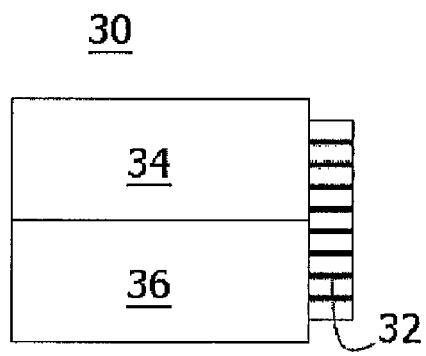
FIG. 1B is a view of a firmware device according to the present invention.

Moreover, in the analytical strip reading apparatus 10 of the present invention, a firmware device 30 is further comprised, as shown in FIG. 1B. The firmware device 30 is electrically connected to an electrical connecting terminal 610 on the mother board 600 and includes a circuit substrate (not shown in Figure) with an electrical connecting terminal 32 formed on one terminal of the circuit substrate for being electrically connected to the electrical connecting terminal 610; meantime, a database sub-module 34 and a process sub-module 36 are further provided on the circuit substrate of the firmware device 30, wherein optical reaction equations of a plurality of analytical strips are saved in the database sub-module 34.

In the following is description of operating process of the analytical strip reading apparatus 10 of the present invention. The monitor 200 is provided on the housing 100 for displaying the status of detection or the test results. The delivering device 300 is configured to support an analytical strip 20 with barcode and move the analytical strip 20 horizontally along a predetermined path so as to deliver the analytical strip 20 into or out of the housing 100; in order for the barcode on the analytical strip 20 to be scanned, the delivering device 300 of the present invention can thus be a transparent carrier board, or a transparent carrier board can be formed at the location where the analytical strip 20 is supported, or an exposing structure can be formed at the location where the analytical strip 20 is placed; thus, the barcode reader 400 provided in the housing 100 can perform a fast and steady scan of barcode on the analytical strip 20 to read the barcode information on the analytical strip 20. The type of barcode on the analytical strip 20 can be a one-dimensional barcode or a two-dimensional barcode, and the barcode information stored in the barcode includes: type of analytical strip, manufacturing date, manufacturing lot number, expiration date, or calibration data of the lot number.

In addition, there are two ways of reading for the barcode reader 400 of the present invention as described below. The first way of reading is as thus: when the analytical strip 20 is delivered into the housing, the delivering device 300 moves the analytical strip 20 along a predetermined path and the barcode information on the analytical strip 20 can be read at the same time in the delivering process; the second way of reading is as thus: when the analytical strip 20 is delivered to the endpoint of the path by the delivering device 300, the barcode information on the analytical strip 20 is then read. Apparently, in the present invention, after the barcode information on the analytical strip 20 is read by the barcode reader 400, the type of the analytical strip, manufacturing date, manufacturing lot number, expiration date, or calibration data of the lot number can be accurately identified according to the contents of the barcode information. Therefore in the process of detection, erroneous usage of improper analytical strip 20 or analytical strip 20 that has passed expiration date can be effectively avoided to ensure the accuracy of the test results. After the analytical strip 20 is verified to be not passing its expiration date, the barcode reader 400 delivers the type information of the analytical strip 20 to the process sub-module 36 on the firmware device 30 for selecting a corresponding optical reaction equation from the database sub-module 34 to perform the following detection procedure.

What is to be further described is that the detection procedure will be different in certain parts for different analytical strips. Take luminescence detection for example, the light emission reaction is self-light emission, and thus no illuminating light source is needed to generate light signal reaction. Yet illumination of a light source is needed for fluorescence detection so that energy can be received to lead to transfer of energy gap for generating light signal reaction. For instance, when the material on the analytical strip 20 is a light emitting material, no illumination of light source device is needed to generate light emission reaction; and for analytical strip 20 of fluorescence color reaction, illumination of light source device is needed for fluorescent material on the analytical strip 20 to generate light signal reaction. Therefore, the analytical strip reading apparatus 10 of the present invention can be selectively provided with light source device (not shown in Figure). Take fluorescence detection for example: when the analytical strip 20 is verified by the barcode reader 400 as an analytical strip 20 of fluorescence color reaction, the analytical strip reading apparatus 10 provides a light source for continuously illuminating the analytical strip 20, and thereafter the reaction signal reader 500 is used for reading and then delivering specific light reaction parameters on the analytical strip 20 to the process sub-module 36 of the firmware device 30.

As described above, in the firmware device 30 of the present invention, database sub-module 34 and process sub-module 36 are comprised. Various types of optical reaction equations of analytical strip 20 are saved in the database sub-module 34, such as optical reaction equations for detecting blood glucose, cholesterol, or hemoglobin. Therefore, when the process sub-module 36 reads the barcode information on the analytical strip 20 via the barcode reader 400 and selects a corresponding optical reaction equation from the database sub-module 34 according to the type of analytical strip 20 in barcode information, the lot number calibration data in barcode information and the specific photoreaction signal read by the reaction signal reader 500 are then loaded in optical reaction equation, and process is performed to come out a test result. What is to be emphasized here is that, the test result in the present invention can be a value after process, and can also be raw data without being processed. And this test result can be displayed by the monitor 200 or delivered via the interface 900. For example, when the analytical strip 20 is a blood glucose analytical strip, after the analytical strip 20 is inserted into the analytical strip reading apparatus 10, the barcode reader 400 automatically reads the barcode information on the analytical strip 20, contents of which include type, manufacturing date, manufacturing lot number, expiration date, or calibration data of lot number; the process sub-module 36 then selects optical reaction equation of blood glucose analytical strip from the database sub-module 34 according to the contents of barcode information; the calibration data of lot and specific photoreaction signal read by the reaction signal reader 500 are then loaded in the equation, and process is performed to come out a test result. The database sub-module 34 in the present embodiment can be a write once memory, and can also be composed of non-volatile memory component, the non-volatile memory component being able to be OTP-ROM, flash memory, EPROM, or EEPROM.

In the aforementioned detection process, the analytical strip reading apparatus 10 will perform determination of all conditions and procedures according to barcode information on the analytical strip 20; for example, when the barcode reader 400 compares the expiration date of the analytical strip 20 read against the date of the detection performed, if the analytical strip 20 has passed the expiration date, the analytical strip reading apparatus 10 will immediately terminate the detection procedure and display related information on the monitor 200. For another example, if the analytical strip 20 is a uric acid analytical strip that has not passed expiration date, after it is inserted into the analytical strip reading apparatus 10, it will be determined as a uric acid analytical strip that has not passed expiration date according to the barcode information read by the barcode reader 400, a corresponding optical reaction equation of uric acid analytical strip will then be selected from the database sub-module 34 and loaded in process sub-module 36, and the calibration data of lot of analytical strip 20 and the photoreaction data acquired by the reaction signal reader 500 are then processed to come out a test result.

Moreover, the analytical strip reading apparatus 10 further comprises an input keyboard 800, via which identification codes of the test subject, such as IC Card number, NHI IC Card number, Social Security Number, or anamnesis number, can be manually inputted and then displayed on the monitor 200 or outputted via the interface 900 at the same time when the test result is outputted for distinguishing the relativity between the test result and the test subject. Furthermore, when the barcode information on the analytical strip 20 cannot be accurately read by the barcode reader 400, information such as the type of the analytical strip 20, manufacturing date, manufacturing lot number, expiration date, or calibration data of lot number can also be manually inputted via the input keyboard 800 for the operation of the analytical strip reading apparatus 10 to continue.

Figure 2:
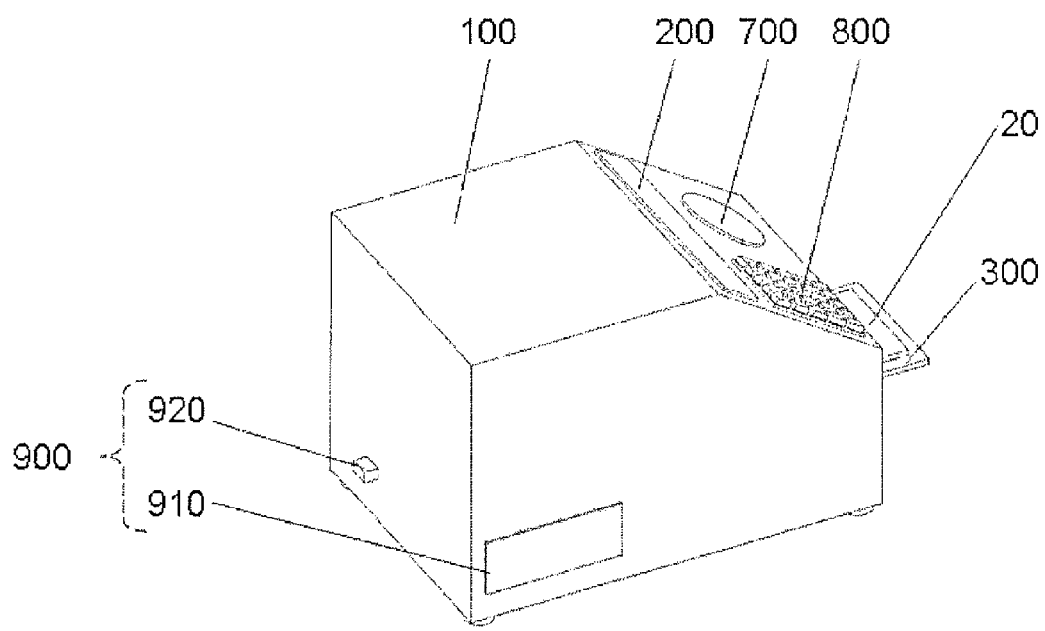
FIG. 2 is a perspective view of another lateral side of an analytical strip reading apparatus according to the present invention.

Then, referring to FIG. 2, which is a view of another lateral side of analytical strip reading apparatus 10 of the present invention. As shown in FIG. 2, an interface 900 is further provided on another lateral side of analytical strip reading apparatus as shown in FIG. 1A for outputting the test result. The interface 900 can be a printer port 910, USB port 920, RS232 port (not shown in Figure), Bluetooth port (not shown in Figure), ZigBee port (not shown in Figure), or Wireless USB port (not shown in Figure), and can be provided according to actual needs. Apparently, the interface 900 is electrically connected to the mother board 600 and provided on the housing 100. What is to be described in particular is that, the printer port 910 can also be directly connected with a printer module and built in the analytical strip reading apparatus 10 to facilitate the user to print out test result instantaneously; the USB port 920 and RS232 port can also be connected with PC to save or analyze the test result; and the Bluetooth port (not shown in Figure), ZigBee port, or Wireless USB port can deliver the test result via corresponding receiver to another apparatus, such as a remote file server.

Figure 3:
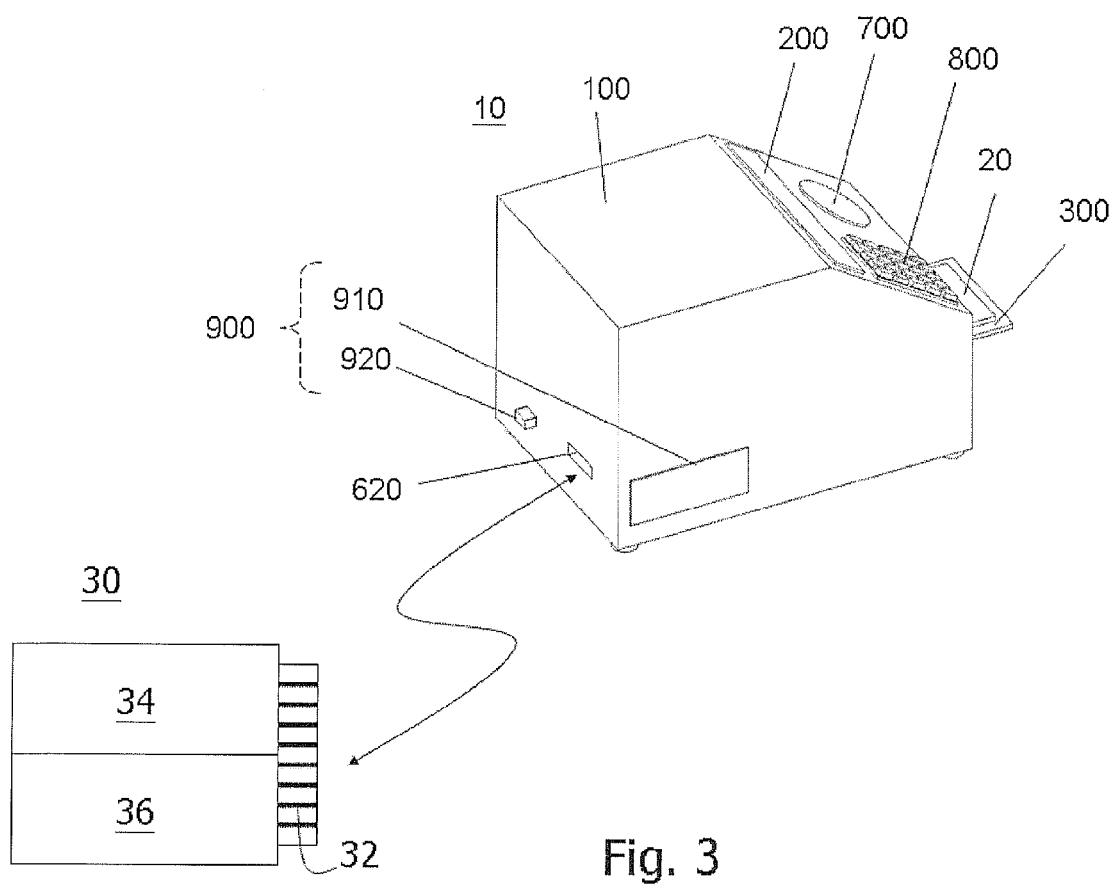
FIG. 3 is a perspective view of another analytical strip reading apparatus according to the present invention.

Reference is now made to FIG. 3, which is a view of another embodiment of analytical strip reading apparatus 10 of the present invention. As shown in FIG. 3, the present embodiment includes a analytical strip reading apparatus 10 and a firmware device 30, wherein structure of analytical strip reading apparatus 10 is the same as that shown in FIG. 1A and the only difference lies in that the firmware device 30 of the present embodiment can be electrically connected to the electrical connecting terminal 610 on the mother board 600 via a connecting slot 620 on the housing 100. Apparently, the electrical connecting terminal 610 of the present embodiment is already provided on one terminal of the mother board 600 (not shown in Figure) and corresponds to a connecting slot 620 on the housing, and therefore the firmware device 30 can be easily and conveniently electrically connected to the electrical connecting terminal 610 on the mother board 600 or removed. When the firmware device 30 in the present embodiment is electrically connected to the electrical connecting terminal 610 on the mother board 600 via the connecting slot 620 on the housing 100, its structure is the same as that of the embodiment shown in FIG. 1A, and therefore operating process of the analytical strip reading apparatus 10 of the present embodiment will not be repeatedly described.

What is to be described in particular is that, the firmware device 30 in the present invention is removably electrically connected to the electrical connecting terminal 610 on the mother board 600, and thus the purpose of updating control program of analytical strip reading apparatus 10 can be achieved by replacing firmware device 30 to ensure the stability of analytical strip reading apparatus 10 and the accuracy of test result. Moreover, the volume of firmware device 30 is quite small, and thus manufacturers can deliver new firmware device 30 to user via Express to eliminate risks generated during and time spent in the transportation of analytical strip reading apparatus 10 and facilitate usage of the users.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the spirit of the present invention should be encompassed by the appended claims.

What is claimed is:

1. An analytical strip reading apparatus, comprising a housing and a monitor provided on the housing, a delivering device for supporting an analytical strip and moving the analytical strip into or out of the housing, a barcode reader provided in the housing for reading barcode information of the analytical strip, a reaction signal reader provided in the housing for reading reaction signal emitted from the analytical strip, and a mother board provided in the housing for being electrically connected to the monitor, the delivering device, the barcode reader, and the reaction signal reader, the analytical strip reading apparatus being characterized by:

further comprising a keyboard provided on the housing and a firmware device provided on the mother board, an identification code being inputted via the keyboard for the firmware device to perform detection, wherein the firmware device includes a database sub-module for saving optical reaction equation of a plurality of types of analytical strips, and a process sub-module, selecting one specific optical reaction equation from the database sub-module according to barcode information on the analytical strip and performing process according to the reaction signal provided by the reaction signal reader to produce a test result of an assay.

2. The analytical strip reading apparatus according to claim 1, wherein barcode information of the analytical strip includes: type of analytical strip, manufacturing date, manufacturing lot number, expiration date, or calibration data recording different manufacturing lot numbers.

3. The analytical strip reading apparatus according to claim 1, wherein the identification code can be selected from the group consisting of: IC Card number, NHI IC Card number, Social Security Number, or anamnesis number.

4. The analytical strip reading apparatus according to claim 1, wherein said database sub-module is a write once memory.

5. The analytical strip reading apparatus according to claim 1, wherein said database sub-module is composed of non-volatile memory.

6. The analytical strip reading apparatus according to claim 5, wherein said non-volatile memory is selected from the group consisting of OTP-ROM, flash memory, EPROM, and EEPROM.

7. The analytical strip reading apparatus according to claim 1, further comprising an interface provided on one lateral side of the housing.

8. The analytical strip reading apparatus according to claim 7, wherein said interface can be selected from the group consisting of: printer port, USB port, RS232 port, Bluetooth port, ZigBee port, and Wireless USB port.

9. An analytical strip reading apparatus with a removable firmware device, comprising an analytical strip reading apparatus and a firmware device, the firmware device comprising a first electrical connecting terminal, a database sub-module, and a process sub-module, said firmware device being removably electrically connected to a second electrical connecting terminal of the analytical strip reading apparatus via the first electrical connecting terminal, wherein the analytical strip reading apparatus is characterized in that:

the database sub-module saves optical reaction equations of a plurality of analytical strips, and after the first electrical connecting terminal of the firmware device acquires an input signal from the second electrical connecting terminal, the process sub-module selects one specific optical reaction equation from the plurality of optical reaction equations saved in the database sub-module and performs process of the specific optical reaction equation.

10. The analytical strip reading apparatus according to claim 9, wherein said database sub-module is a write once memory.

11. The analytical strip reading apparatus according to claim 9, wherein said database sub-module is composed of non-volatile memory.

12. The analytical strip reading apparatus according to claim 11, wherein said non-volatile memory is selected from the group consisting of OTP-ROM, flash memory, EPROM, and EEPROM.

13. The analytical strip reading apparatus according to claim 9, wherein the input signal includes a barcode information and a specific reaction signal.

14. The analytical strip reading apparatus according to claim 9, further comprising an interface provided on one lateral side of the housing.

15. The analytical strip reading apparatus according to claim 14, wherein said interface can be selected from the group consisting of: printer port, USB port, RS232 port, Bluetooth port, ZigBee port, and Wireless USB port.

16. An analytical strip reading apparatus with a removable firmware device, comprising a housing and a monitor provided on the housing, a delivering device for supporting an analytical strip and moving the analytical strip into or out of the housing, a barcode reader provided in the housing for reading barcode information of the analytical strip, a reaction signal reader provided in the housing for reading photoreaction signal of the analytical strip, a mother board provided in the housing for being electrically connected to the monitor, the delivering device, the barcode reader, and the reaction signal reader, one end of the mother board being provided with a first electrical connecting terminal, and a firmware device, the firmware device comprising a second electrical connecting terminal, a database sub-module, and a process sub-module, the firmware device being removably electrically connected to the first electrical connecting terminal of the mother board via the second electrical connecting terminal, wherein the analytical strip reading apparatus is characterized in that:

the database sub-module saves optical reaction equations of a plurality of analytical strips, and after the second electrical connecting terminal acquires an input signal from the first electrical connecting terminal, the process sub-module selects one specific optical reaction equation from the plurality of optical reaction equations saved in the database sub-module and performs process of the specific optical reaction equation.

17. The analytical strip reading apparatus according to claim 16, wherein said database sub-module is a write once memory.

18. The analytical strip reading apparatus according to claim 16, wherein said database sub-module is composed of non-volatile memory.

19. The analytical strip reading apparatus according to claim 18, wherein said non-volatile memory is selected from the group consisting of OTP-ROM, flash memory, EPROM, and EEPROM.

20. The analytical strip reading apparatus according to claim 16, wherein the input signal includes a barcode information provided by the barcode reader and a specific reaction signal provided by the reaction signal reader.

21. The analytical strip reading apparatus according to claim 16, further comprising an interface provided on one lateral side of the housing.

22. The analytical strip reading apparatus according to claim 21, wherein said interface can be selected from the group consisting of: printer port, USB port, RS232 port, Bluetooth port, ZigBee port, and Wireless USB port.

* * * * *